(12) United States Patent
Bai et al.

(10) Patent No.: US 12,383,596 B1
(45) Date of Patent: Aug. 12, 2025

(54) CHINESE HERBAL MEDICINE COMPOSITION FOR BOOSTING IMMUNITY, AND PREPARATION METHOD AND USE THEREOF

(71) Applicants: Guangzhou University of Chinese Medicine, Guangdong (CN); Zhongkefu Moxibustion (Hunan) Health Tech Co., Ltd., Changde (CN)

(72) Inventors: Yunlong Bai, Guangzhou (CN); Yongchao Ning, Guangzhou (CN); Wei Zhang, Guangzhou (CN); Yan Yu, Guangzhou (CN)

(73) Assignees: Guangzhou University of Chinese Medicine, Guangdong (CN); Zhongkefu Moxibustion (Hunan) Health Tech Co., Ltd., Changde (CN)

( * ) Notice: Subject to any disclaimer, the term of this patent is extended or adjusted under 35 U.S.C. 154(b) by 0 days.

(21) Appl. No.: 18/947,697

(22) Filed: Nov. 14, 2024

(30) Foreign Application Priority Data

Jul. 2, 2024 (CN) .......................... 202410877540.1

(51) Int. Cl.
| | | |
|---|---|---|
| *A61K 36/752* | (2006.01) | |
| *A61K 36/284* | (2006.01) | |
| *A61K 36/64* | (2006.01) | |
| *A61K 36/738* | (2006.01) | |
| *A61K 36/815* | (2006.01) | |
| *A61K 36/88* | (2006.01) | |
| *A61P 37/04* | (2006.01) | |

(52) U.S. Cl.
CPC .......... *A61K 36/752* (2013.01); *A61K 36/284* (2013.01); *A61K 36/64* (2013.01); *A61K 36/738* (2013.01); *A61K 36/815* (2013.01); *A61K 36/88* (2013.01); *A61P 37/04* (2018.01); *A61K 2236/15* (2013.01); *A61K 2236/331* (2013.01); *A61K 2236/333* (2013.01); *A61K 2236/51* (2013.01); *A61K 2236/53* (2013.01)

(58) Field of Classification Search
None
See application file for complete search history.

(56) References Cited

FOREIGN PATENT DOCUMENTS

CN 117959374 A 5/2024

OTHER PUBLICATIONS

Chen (CN 10358454 A—English translation)—Feb. 2014.*
Liu (CN 1857690 A—English translation)—Nov. 2006.*
Huang et al: "Effect of Pingwei Powder on Part on Immunological Function in Rats with Syndrom of Dampness Blocking Spleen and Stomach", Journal on Traditional Chinese Medicine, vol. 48, No. 8, p. 730-732, 2007.
Liu et al: "Twenty cases of HIV infectors without symptoms at early stage treated by purulent moxibustion", World Journal of Acupuncture-Mosibustion (WJAM), vol. 23, No. 1, p. 61-64, Mar. 30, 2013.
Yu et al: "Effects of Moxibustion Therapy on Preventing and Treating Side Effects from Chemotherapy of Malignant Tumor Patients", J. Acupunct. Tuina. Sci., vol. 9, No. 6, p. 351-353, 2011.

* cited by examiner

*Primary Examiner* — Susan Hoffman
(74) *Attorney, Agent, or Firm* — WCF IP

(57) ABSTRACT

A Chinese herbal medicine composition for boosting immunity, and a preparation method and use thereof are provided, belonging to the technical field of pharmaceutical preparations. The Chinese herbal medicine composition for boosting immunity is prepared with Lingnan authentic medicinal materials (Exocarpium *Citri Grandis*, dried tangerine peel, and *Rhizoma Atractylodis*) as a main drug, which is supplemented with affordable medicinal materials (*Rosa roxburghii* fruit, *Fructus Lycii*, *Herba Cistanches*, and saffron). The Chinese herbal medicine composition can be used in conjunction with moxibustion therapy to effectively improve the immunity of human body and relieve fatigue. Moreover, optimization of the preparation method can further improve a use effect of the drugs.

5 Claims, No Drawings

CHINESE HERBAL MEDICINE COMPOSITION FOR BOOSTING IMMUNITY, AND PREPARATION METHOD AND USE THEREOF

CROSS REFERENCE TO RELATED APPLICATION

This patent application claims the benefit and priority of Chinese Patent Application No. 2024108775401, filed with the China National Intellectual Property Administration on Jul. 2, 2024, the disclosure of which is incorporated by reference herein in its entirety as part of the present application.

TECHNICAL FIELD

The present disclosure belongs to the technical field of pharmaceutical preparations, and particularly relates to a Chinese herbal medicine composition for boosting immunity, and a preparation method and use thereof.

BACKGROUND

Immunity, a human body's ability to resist pathogens and foreign substances, is the basis for maintaining health. The immunity includes innate immunity and acquired immunity, where the former is a human body's natural defense mechanism, while the latter is a specific response produced by the human body after contact with pathogens. The level of immunity is affected by many factors, such as age, genetics, nutrition, environment, psychology, and lifestyle habits. Low immunity makes people unable to effectively resist external pathogens and foreign substances, leading to susceptibility to infection and inflammation, and then increasing the risk and severity of infection. In addition, the low immunity can easily lead to the accelerated occurrence and development of cancer, making it impossible for human body to effectively eliminate abnormal cells.

Moxibustion therapy is a traditional Chinese medical technology that achieves curing and controlling diseases through the heat generated by moxibustion mist. Moxibustion has been used for disease prevention and health care for a long time in China, and not only cures diseases but also has the effects of disease prevention, health care, and longevity. The health-care effects of moxibustion have been proven by a large number of clinical observations and experimental studies, and can adjust and improve the human body's immunity and enhance disease resistance.

Moreover, it has long been recorded that moxibustion is used for health care, disease prevention, and longevity. The Assemble of Acupuncture and Moxibustion wrote by GAO Wu in the Ming Dynasty has mentioned that "Acupuncture and moxibustion before illness is called Routine, Routine means to prevent the diseases before they arrive". "Routine moxibustion" is a health-care moxibustion method used in ancient times, and refers to the use of moxibustion in advance before the human body is disease-free or before the disease occurrence. This method stimulates the meridians and blood to enhance the human body's disease resistance and resilience, thereby preventing the occurrence and development of diseases and achieving prevention as treatment. This is an important manifestation of the Chinese medicine idea of "treating illness before it occurs".

In the journal document ("Twenty cases of HIV infectors without symptoms at early stage treated by purulent moxibustin", Liu Z et al. [J]. *World J of Acupuncture-Moxibustion*, 2013, 23 (1): 61-64), 20 cases of HIV infectors without symptoms at early stage were treated with purulent moxibustion aiming at Zusanli, Xuanzhong, and Guanyuan acupoints, which significantly improved the patients' clinical symptoms and signs, increased the Karnofsky score, quality of life score, and then increased $CD^{4+}$ T lymphocyte counts.

In the journal document ("Effects of Moxibustion Therapy on Preventing and Treating Side Effects from Chemotherapy of Malignant Tumor Patients", Fan Y et al. [J]. *J Acupunct Tuina Sci*, 2011, 9 (6): 351-353), moxibustion was conducted to treat 23 patients with respiratory and digestive system malignancies who were suffering from chemotherapy-related toxicity and side effects. It was found that moxibustion could increase the total white blood cell count and immunoglobulin and had a better therapeutic effect than that of batyl alcohol.

Existing technology shows that moxibustion can improve the human body's immunity by affecting immune cells, immune regulatory factors, and immunoglobulins. The effect of moxibustion therapy is not only related to a moxibustion technique, but also has a lot to do with a moxibustion prescription used. However, in-depth research on the moxibustion prescription has not been conducted in the prior art.

Authentic medicinal materials are traditionally recognized Chinese medicinal materials that are grown in the best growing environment and regions and have high quality and efficacy for clinical applications. Authenticity research of the Chinese medicinal materials is a key to ensuring the quality of medicinal materials and their clinical efficacy. Lingnan region is located in the tropical and subtropical regions, with hot and rainy weather all year round and rich geothermal and hydrothermal resources. Due to a unique geographical environment, this region has bred a variety of local medicinal materials, and some of Lingnan authentic medicinal materials have the effect of enhancing immunity.

Based on the above contents, the present disclosure fully considers the characteristics of Lingnan Chinese herbal medicine. A Chinese herbal medicine composition for boosting immunity is prepared with Lingnan authentic medicinal materials (Exocarpium *Citri Grandis*, dried tangerine peel, and *Rhizoma Atractylodis*) as a main drug, which is supplemented with affordable medicinal materials (*Rosa roxburghii* fruit, *Fructus Lycii, Herba Cistanches*, and saffron). The Chinese herbal medicine composition can be used in conjunction with moxibustion therapy to effectively improve the immunity of human body and relieve fatigue. Moreover, optimization of the preparation method can further improve a use effect of the drugs.

SUMMARY

In view of the problems existing in the prior art, an objective of the present disclosure is to provide a Chinese herbal medicine composition for boosting immunity, and a preparation method and use thereof. The Chinese herbal medicine composition for boosting immunity is prepared with Lingnan authentic medicinal materials (Exocarpium *Citri Grandis*, dried tangerine peel, and *Rhizoma Atractylodis*) as a main drug, which is supplemented with affordable medicinal materials (*Rosa roxburghii* fruit, *Fructus Lycii, Herba Cistanches*, and saffron). The Chinese herbal medicine composition can be used in conjunction with moxibustion therapy to effectively improve the immunity of human body and relieve fatigue. Moreover, optimization of the preparation method can further improve a use effect of the drugs.

In order to achieve the above objective, a first aspect of the present disclosure is to provide a preparation method of a Chinese herbal medicine composition for boosting immunity, where the Chinese herbal medicine composition for boosting immunity includes the following components in parts by weight: 5 parts to 15 parts of Exocarpium *Citri Grandis*, 10 parts to 30 parts of dried tangerine peel, 5 parts to 20 parts of *Rhizoma Atractylodis*, 10 parts to 15 parts of *Rosa roxburghii* fruit, 10 parts to 30 parts of *Fructus Lycii*, 15 parts to 25 parts of *Herba Cistanches*, and 5 parts to 15 parts of saffron; and the preparation method includes:
1) crushing the Exocarpium *Citri Grandis*, the dried tangerine peel, and the *Rhizoma Atractylodis* to obtain a powder 1, conducting extraction with an 80% to 95% ethanol solution, and then conducting filtration to obtain an alcohol extract;
2) crushing the *Rosa roxburghii* fruit, the *Fructus Lycii*, the *Herba Cistanches*, and the saffron to obtain a powder 2, conducting extraction with water, adding ethanol to allow alcohol precipitation, and then collecting an obtained supernatant; and
3) combining the alcohol extract obtained in step 1) and the supernatant obtained in step 2), and then drying an obtained mixture to obtain the Chinese herbal medicine composition for boosting immunity.

Preferably, the crushing in steps 1) and 2) is conducted to a particle size of 100 mesh to 300 mesh.

Preferably, the ethanol solution and the powder 1 are at a volume-to-mass ratio of (5-20) mL:1 g, and the extraction is conducted at 10° C. to 40° C. for 10 h to 60 h in step 1).

Preferably, the water and the powder 2 are at a volume-to-mass ratio of (5-30) mL:1 g, and the extraction is conducted at 40° C. to 80° C. for 1 h to 5 h in step 2).

Preferably, the ethanol in a system obtained during the alcohol precipitation in step 2) has a volume concentration of 60% to 90%.

Preferably, the drying in step 3) is selected from the group consisting of heating drying, freeze drying, and natural drying.

A second aspect of the present disclosure is to provide a Chinese herbal medicine composition for boosting immunity prepared by the preparation method.

A third aspect of the present disclosure is to provide use of the Chinese herbal medicine composition for boosting immunity in preparation of a product for enhancing the immunity.

Preferably, the product for enhancing the immunity includes a health-care moxibustion, a cigarette, and an aromatherapy.

A fourth aspect of the present disclosure is to provide a health-care moxibustion, including the Chinese herbal medicine composition for boosting immunity.

Preferably, a process of the health-care moxibustion includes conducting medicine-separated moxibustion on the Shenque acupoint.

Exocarpium *Citri Grandis* and dried tangerine peel are two of the eight major Lingnan authentic traditional Chinese medicines with an extremely high medicinal value. The Exocarpium *Citri Grandis* is a special Chinese medicinal material mainly produced in Huazhou, containing flavonoids, polysaccharides, volatile oils, coumarins and other bioactive substances. This component has medicinal functions including relieving cough and reducing sputum, anti-thrombosis, anti-inflammation, prevention and treatment of myocardial damage caused by diabetic cardiomyopathy, and protection of liver and lungs, as well as health functions such as anti-oxidation, lowering blood glucose, regulating blood lipids, enhancing immunity, and anti-fatigue. The dried tangerine peel contains rich bioactive substances, such as flavonoids, alkaloids, volatile oils, and polysaccharides, and has the effects of anti-inflammation, improving immunity, promoting digestion, protecting the liver, relieving cough and reducing asthma, and anti-tumor. *Rhizoma Atractylodis* is also a Lingnan authentic medicinal material, and shows the effects of drying dampness and strengthening the spleen, dispelling wind and cold, reducing swelling and relieving pain, regulating immunity, and strengthening the spleen and stopping diarrhea.

In addition, *Herba Cistanches* has the effects of immune regulation, anti-oxidation, anti-aging, anti-fatigue, neuroprotection, and liver protection. Saffron can promote blood circulation, improve blood circulation, prevent and treat cardiovascular diseases, relieve depression and calm the mind, improve sleep quality, relieve stress and anxiety, improve mood and memory, and enhance immunity. *Rosa roxburghii* fruit can enhance immunity, exert anti-oxidation and anti-aging, improve stomach and digestion, and stop diarrhea. *Fructus Lycii* is rich in antioxidants that delay aging, exhibit anti-fatigue, prevent atherosclerosis and heart disease, and enhance immune cell activity.

The present disclosure is based on Lingnan authentic medicinal materials (Exocarpium *Citri Grandis*, dried tangerine peel, and *Rhizoma Atractylodis*) as a main drug, which is supplemented with affordable medicinal materials (*Rosa roxburghii* fruit, *Fructus Lycii*, *Herba Cistanches*, and saffron). A synergistic effect of these medicinal materials can enhance a function of the immune system.

Compared with the prior art, beneficial effects of the present disclosure are as follows:
1. In the present disclosure, the Chinese herbal medicine composition for boosting immunity is prepared with Lingnan authentic medicinal materials (Exocarpium *Citri Grandis*, dried tangerine peel, and *Rhizoma Atractylodis*) as a main drug, which is supplemented with affordable medicinal materials (*Rosa roxburghii* fruit, *Fructus Lycii*, *Herba Cistanches*, and saffron). The Chinese herbal medicine composition can be used in conjunction with moxibustion therapy to effectively improve the immunity of human body and relieve fatigue. Moreover, optimization of the preparation method can further improve a use effect of the drugs.
2. In the present disclosure, the Chinese herbal medicine composition for boosting immunity uses affordable medicinal materials, thereby reducing the cost of use and showing desirable economic benefits.
3. In the present disclosure, the Chinese herbal medicine composition for boosting immunity can be used for health-care moxibustion. Medicine-separated moxibustion of the Shenque acupoint can effectively relieve fatigue and produce a positive stimulation effect on the immune system.

DETAILED DESCRIPTION OF THE EMBODIMENTS

It should be noted that the medicinal materials used in the present disclosure are ordinary commercially-available products, and sources of the raw materials are not specifically limited.

The following sources of raw materials are provided for illustrative purposes:

Example 1

A preparation method of a Chinese herbal medicine composition for boosting immunity The Chinese herbal medicine composition for boosting immunity included the following components in parts by weight: 10 parts of Exocarpium *Citri Grandis,* 20 parts of dried tangerine peel, 15 parts of *Rhizoma Atractylodis,* 13 parts of *Rosa roxburghii* fruit, 20 parts of *Fructus Lycii,* 20 parts of *Herba Cistanches,* and 10 parts of saffron; and the preparation method included:
1) a powder 1 was obtained by crushing the Exocarpium *Citri Grandis,* the dried tangerine peel, and the *Rhizoma Atractylodis* to 200 mesh, and the powder 1 was mixed with a 90% (volume concentration) ethanol solution at a volume-to-mass ratio of 10 mL:1 g to allow extraction at room temperature (25° C.) for 40 h, and then filtration was conducted to obtain an alcohol extract;
2) a powder 2 was obtained by crushing the *Rosa roxburghii* fruit, the *Fructus Lycii,* the *Herba Cistanches,* and the saffron to 200 mesh, and the powder 2 was mixed with water at a volume-to-mass ratio of 20 mL:1 g to allow extraction at 60° C. for 3 h, ethanol was added such that the ethanol in an obtained system had a volume concentration of 75% to allow alcohol precipitation, allowed to stand and filtered, and then an obtained supernatant was collected; and
3) the alcohol extract obtained in step 1) and the supernatant obtained in step 2) were combined, and then an obtained mixture was subjected to freeze drying to obtain the Chinese herbal medicine composition for boosting immunity.

Example 2

A preparation method of a Chinese herbal medicine composition for boosting immunity The Chinese herbal medicine composition for boosting immunity included the following components in parts by weight: 5 parts of Exocarpium *Citri Grandis,* 30 parts of dried tangerine peel, 5 parts of *Rhizoma Atractylodis,* 10 parts of *Rosa roxburghii* fruit, 30 parts of *Fructus Lycii,* 15 parts of *Herba Cistanches,* and 15 parts of saffron; and the preparation method included:
1) a powder 1 was obtained by crushing the Exocarpium *Citri Grandis,* the dried tangerine peel, and the *Rhizoma Atractylodis* to 100 mesh, and the powder 1 was mixed with a 95% (volume concentration) ethanol solution at a volume-to-mass ratio of 6 mL:1 g to allow extraction at room temperature (25° C.) for 60 h, and then filtration was conducted to obtain an alcohol extract;
2) a powder 2 was obtained by crushing the *Rosa roxburghii* fruit, the *Fructus Lycii,* the *Herba Cistanches,* and the saffron to 300 mesh, and the powder 2 was mixed with water at a volume-to-mass ratio of 30 mL:1 g to allow extraction at 50° C. for 2 h, ethanol was added such that the ethanol in an obtained system had a volume concentration of 60% to allow alcohol precipitation, allowed to stand and filtered, and then an obtained supernatant was collected; and
3) the alcohol extract obtained in step 1) and the supernatant obtained in step 2) were combined, and then an obtained mixture was subjected to freeze drying to obtain the Chinese herbal medicine composition for boosting immunity.

Example 3

A preparation method of a Chinese herbal medicine composition for boosting immunity The Chinese herbal medicine composition for boosting immunity included the following components in parts by weight: 15 parts of Exocarpium *Citri Grandis,* 10 parts of dried tangerine peel, 20 parts of *Rhizoma Atractylodis,* 15 parts of *Rosa roxburghii* fruit, 10 parts of *Fructus Lycii,* 25 parts of *Herba Cistanches,* and 5 parts of saffron; and the preparation method included:
1) a powder 1 was obtained by crushing the Exocarpium *Citri Grandis,* the dried tangerine peel, and the *Rhizoma Atractylodis* to 300 mesh, and the powder 1 was mixed with a 80% (volume concentration) ethanol solution at a volume-to-mass ratio of 20 mL:1 g to allow extraction at room temperature (25° C.) for 10 h, and then filtration was conducted to obtain an alcohol extract;
2) a powder 2 was obtained by crushing the *Rosa roxburghii* fruit, the *Fructus Lycii,* the *Herba Cistanches,* and the saffron to 100 mesh, and the powder 2 was mixed with water at a volume-to-mass ratio of 5 mL:1 g to allow extraction at 80° C. for 5 h, ethanol was added such that the ethanol in an obtained system had a volume concentration of 90% to allow alcohol precipitation, allowed to stand and filtered, and then an obtained supernatant was collected; and
3) the alcohol extract obtained in step 1) and the supernatant obtained in step 2) were combined, and then an obtained mixture was subjected to freeze drying to obtain the Chinese herbal medicine composition for boosting immunity.

Comparative Example 1

Except that the *Herba Cistanches* was replaced by *Gynura procumbens,* the rest steps were the same as those in Example 1.

Comparative Example 2

Except that 15 parts of Exocarpium *Citri Grandis,* 30 parts of dried tangerine peel, and 0 parts of *Rhizoma Atractylodis* were used, the rest steps were the same as those in Example 1.

Comparative Example 3

Except that 0 parts of Exocarpium *Citri Grandis,* 0 parts of dried tangerine peel, and 45 parts of *Rhizoma Atractylodis* were used, the rest steps were the same as those in Example 1.

Comparative Example 4

Except that 70% (volume concentration) ethanol solution was used in step 1), the rest steps were the same as those in Example 1.

Comparative Example 5

Except that a precipitate was collected after allowing to stand and filtering in step 2) instead of the supernatant, the rest steps were the same as those in Example 1.

Test Example

1. Preparation of health-care moxibustion (i.e., medicine cake): the Chinese herbal medicine compositions for boosting immunity obtained in Examples 1 to 3 and Comparative Examples 1 to 5 were separately ground into a fine powder, which was mixed with fresh ginger juice at a mass ratio of 2:1 to form a paste, and then pressed into medicine cakes with a diameter of 0.8 cm and a thickness of 0.3 cm by a mold. At the same time, flour and the fresh ginger juice were mixed into a paste in a mass ratio of 2:1, and then pressed into a medicine cake with a diameter of 0.8 cm and a thickness of 0.3 cm as a sham medicine cake.

2. Experimental animals: 110 SPF-grade adult SD rats, weighing 200±20 g, half male and half female, were provided by Liaoning Changsheng Biotechnology Co., Ltd., with production license number: SCXK (Liao) 2010-0001. The rats were randomly divided into 11 groups, namely a blank group, a model group, a sham medicine cake group, and Example 1 to 3 groups and Comparative Example 1 to 5 groups. After 7 d of adaptive feeding, rats other than the blank group were subjected to chronic fatigue syndrome (CFS) modeling. The rats were forced to swim for 15 min every day in a metal cylinder with a diameter of 35 cm and a height of 45 cm at a water depth of 30 cm under room temperature (24° C. to 28° C.) for 21 consecutive days. After modeling, behavioral tests (open field test OFT and tail suspension test TST) showed that the modeling was successful.

3. Intervention method: the intervention treatment started on the 2rd day after the modeling. The blank group and the model group did not receive any treatment; for the Example 1 to 3 groups, Comparative Example 1 to 5 groups, and sham medicine cake group, the Shenque acupoint of the rat was selected, the hair at the acupoint was removed, and the corresponding medicine cake and moxa stick were placed (the moxa was prepared into a conical moxa stick with a bottom diameter of 0.5 cm and a height of 0.5 cm, and placed on the medicine cake). The moxa stick was ignited, and replaced with a new one after burning out, where moxibustion was conducted on each acupoint 3 times, 1 time a day, for 10 consecutive days.

4. OFT and TST:

The rats in each group were subjected to OFT and TST, and a number of horizontal grids crossed (grids/4 min), a number of standing times (times/4 min), a movement distance (m/4 min), a number of struggling times (times/4 min), and an immobility time (s/4 min) were statistically analyzed (Table 1).

TABLE 1

OFT and TST results of rats in each group

| Group | OFT | | | TST | |
|---|---|---|---|---|---|
| | Number of horizontal grids crossed | Number of standing times | Movement distance | Number of struggling times | Immobility time |
| Blank group | 59.7 ± 16.9 | 23.1 ± 6.2 | 36.45 ± 15.56 | 34.5 ± 7.3 | 73.6 ± 14.2 |
| Model group | 27.2 ± 14.3** | 8.2 ± 4.5** | 20.11 ± 10.45* | 11.4 ± 5.1** | 128.2 ± 30.6** |
| Sham medicine cake group | 32.9 ± 10.4** | 9.3 ± 3.8** | 23.23 ± 8.76* | 15.8 ± 6.4** | 119.3 ± 28.8** |
| Example 1 | 60.1 ± 18.2## | 21.2 ± 3.6## | 36.01 ± 6.78# | 32.1 ± 5.2## | 75.5 ± 15.4## |
| Example 2 | 58.5 ± 17.1## | 19.7 ± 2.8## | 34.98 ± 6.21# | 28.7 ± 4.9## | 78.3 ± 15.8## |
| Example 3 | 57.1 ± 16.0## | 18.4 ± 2.9## | 33.37 ± 5.69# | 30.4 ± 5.1## | 80.2 ± 16.3## |
| Comparative Example 1 | 44.0 ± 15.4*# | 13.3 ± 3.3*# | 26.11 ± 7.12* | 20.8 ± 5.4*# | 98.4 ± 21.4*# |
| Comparative Example 2 | 43.6 ± 14.8*# | 13.5 ± 2.9*# | 25.22 ± 7.34* | 18.4 ± 5.0** | 104.7 ± 24.3*# |
| Comparative Example 3 | 39.1 ± 13.7*# | 11.3 ± 2.7* | 24.32 ± 8.01* | 17.1 ± 4.8** | 108.7 ± 25.7*# |
| Comparative Example 4 | 45.3 ± 14.2*# | 14.4 ± 3.0*# | 26.73 ± 7.83* | 21.4 ± 5.5*# | 96.4 ± 17.8*# |
| Comparative Example 5 | 38.2 ± 15.1*# | 10.5 ± 2.7* | 24.01 ± 7.04* | 18.0 ± 4.6** | 110.3 ± 19.3*# |

NOTE:
*indicated $P < 0.05$ compared with the blank group;
**indicated $P < 0.01$ compared with the blank group;
indicated $P < 0.05$ compared with the model group;
indicated $P < 0.01$ compared with the model group.

As shown in Table 1, there were significant differences in the behaviors between the model group and the blank group, indicating that the CFS rat model was successfully established. There was no significant difference between the sham medicine cake group and the model group; the Example 1 to 3 groups were close to the blank group and had no significant difference, but had significant difference with the model group; the Comparative Example 1 to 5 groups were close to the model group and had significant difference with the blank group. In general, Example 1 to 3 groups could effectively improve fatigue of CFS rats; while the sham medicine cake group and Comparative Example 1 to 5 groups had a limited improvement in fatigue of CFS rats, or the improvement was significantly inferior to that of Example 1 to 3 groups.

The difference between Comparative Examples 1 to 3 and Example 1 was that the types of medicinal materials were different; the difference between Comparative Example 4 and Example 1 was that the concentration of the ethanol solution in step 1) was different; the difference between Comparative Example 5 and Example 1 was that the precipitate (water-soluble component, polysaccharide) was obtained instead of the supernatant (alcohol-soluble component, flavonoids, and polyphenols) in step 2). The concentration of the ethanol solution in step 1) might affect the extracted active components (the specific types and proportions of alcohol-soluble components and water-soluble components); the precipitate in step 2) was water-soluble polysaccharides, and the supernatant was mainly composed of fat-soluble components such as flavonoids and polyphenols, such that there were huge differences in composition and performance of the two parts.

As shown in Table 1, the type of medicinal materials and the preparation process in the Chinese herbal medicine composition disclosed in the present disclosure had a great influence on the fatigue-relieving effect.

Replacing the *Herba Cistanches* with *Gynura procumbens*, or using only the Exocarpium *Citri Grandis* and dried tangerine peel, or using only the *Rhizoma Atractylodis* could all lead to significant performance degradation. In particular, the total amount of Exocarpium *Citri Grandis*, dried tangerine peel, and *Rhizoma Atractylodis* used in Comparative Examples 2 to 3 was the same as that in Example 1, except that one, two, or three of the three medicinal materials were used. This difference in effect showed that the combined use of Exocarpium *Citri Grandis*, dried tangerine peel, and *Rhizoma Atractylodis* had a synergistic effect.

The ethanol solution defined in step 1) was conducive to obtaining a Chinese herbal medicine composition with better effects; while the alcohol-soluble components of *Rosa roxburghii* fruit, *Fructus Lycii*, *Herba Cistanches*, and saffron collected in step 2) had better technical effects than collecting their water-soluble components.

5. Thymus Index, Spleen Index, and T Cell Subset Test

After the OFT and TST, the rats were weighed and then sacrificed. Their spleen and thymus were removed in a sterile environment and weighed to calculate the thymus index and spleen index (weight of thymus or spleen in mg/body weight in g), as shown in Table 2.

At the same time, the T cell subsets in the spleen of rats were tested. Specifically, a single cell suspension of spleen tissue of each group of rats was prepared by grinding, and the red blood cells were lysed by adding a red blood cell lysis solution, washed, centrifuged, and washed with PBS for multiple times. Fluorescein isothiocyanate-labeled anti-rat CD3 monoclonal antibody, phycoerythrin-labeled anti-rat CD4 monoclonal antibody, and allophycocyanin-labeled anti-rat CD8 monoclonal antibody were added and incubated at 4° C. for 1 h. The cells were washed with PBS 3 times, mixed with PBS, and detected by a flow cytometer (model: BD FACSCanto II). The results were shown in Table 3.

TABLE 2

Thymus index and spleen index of rats in each group

| Group | Thymus index | Spleen index |
| --- | --- | --- |
| Blank group | 0.301 ± 0.016 | 0.620 ± 0.018 |
| Model group | 0.164 ± 0.011 | 0.386 ± 0.012 |
| Sham medicine cake group | 0.182 ± 0.012* | 0.411 ± 0.011 |
| Example 1 | 0.291 ± 0.015## | 0.602 ± 0.017## |
| Example 2 | 0.261 ± 0.014## | 0.585 ± 0.018## |
| Example 3 | 0.273 ± 0.014## | 0.596 ± 0.016## |
| Comparative Example 1 | 0.221 ± 0.011 | 0.467 ± 0.014*# |
| Comparative Example 2 | 0.227 ± 0.012*# | 0.479 ± 0.015*# |
| Comparative Example 3 | 0.203 ± 0.013** | 0.455 ± 0.016* |
| Comparative Example 4 | 0.218 ± 0.011*# | 0.502 ± 0.013*# |
| Comparative Example 5 | 0.209 ± 0.011*# | 0.480 ± 0.014*# |

NOTE:
*indicated $P < 0.05$ compared with the blank group;
**indicated $P < 0.01$ compared with the blank group;
indicated $P < 0.05$ compared with the model group;
indicated $P < 0.01$ compared with the model group.

TABLE 3

T cell subsets of rats in each group

| Group | $CD^{3+}$ | $CD^{4+}$ | $CD^{8+}$ | CD4/CD8 |
| --- | --- | --- | --- | --- |
| Blank group | 72.15 ± 1.83 | 45.11 ± 2.13 | 26.23 ± 1.42 | 1.72 ± 0.03 |
| Model group | 47.34 ± 1.42** | 31.22 ± 1.51** | 30.11 ± 1.67* | 1.04 ± 0.04** |
| Sham medicine cake group | 50.55 ± 1.51** | 34.14 ± 1.62** | 29.76 ± 1.68* | 1.15 ± 0.06** |
| Example 1 | 70.23 ± 1.79## | 45.09 ± 2.04## | 27.02 ± 1.52# | 1.67 ± 0.03## |
| Example 2 | 66.34 ± 1.80## | 44.20 ± 2.00## | 26.98 ± 1.52# | 1.64 ± 0.03## |
| Example 3 | 68.11 ± 1.77## | 43.25 ± 1.94## | 27.38 ± 1.54# | 1.58 ± 0.04# |
| Comparative Example 1 | 57.32 ± 1.72** | 37.03 ± 1.84*# | 28.88 ± 1.62* | 1.28 ± 0.04* |
| Comparative Example 2 | 56.11 ± 1.70*# | 36.45 ± 1.79* | 29.02 ± 1.61* | 1.26 ± 0.03* |
| Comparative Example 3 | 54.04 ± 1.68* | 36.08 ± 1.76* | 29.34 ± 1.64* | 1.23 ± 0.04* |
| Comparative Example 4 | 58.45 ± 1.72*# | 37.67 ± 1.80*# | 28.76 ± 1.58* | 1.31 ± 0.03* |
| Comparative Example 5 | 55.22 ± 1.71* | 35.37 ± 1.75* | 29.12 ± 1.60* | 1.21 ± 0.03* |

NOTE:
*indicated $P < 0.05$ compared with the blank group;
**indicated $P < 0.01$ compared with the blank group;
indicated $P < 0.05$ compared with the model group;
indicated $P < 0.01$ compared with the model group.

As shown in Tables 2 to 3, the thymus index, spleen index, and T cell subset distribution of the model group were significantly different from those of the blank group, indicating that the immune organs of the rats atrophied and degenerated and the T cell subsets were disordered after modeling. There was no significant difference between the sham medicine cake group and the model group, indicating that the efficacy of moxibustion alone on the sham medicine cake was not significant. The Example 1 to 3 groups were close to the blank group and had no significant difference, but had significant difference with the model group; the Comparative Example 1 to 5 groups were close to the model group and had significant difference with the blank group. In general, both Examples 1 to 3 and Comparative Examples 1 to 5 could delay the atrophy and degeneration of rat immune organs, regulate and correct the disordered state of T cell subsets, and enhance immunity, and Examples 1 to 3 were superior to Comparative Examples 1 to 5.

The data in Tables 2 to 3 also showed that in the Chinese herbal medicine composition disclosed in the present disclosure, the type of medicinal materials and the preparation process had a great influence on the immune-enhancing effect.

The *Herba Cistanches* instead of *Gynura procumbens*, or the combined use of Exocarpium *Citri Grandis*, dried tangerine peel, and *Rhizoma Atractylodis* was beneficial to improve immunity. Moreover, the ethanol solution defined in step 1) was conducive to obtaining a Chinese herbal medicine composition with better effects; while the alcohol-soluble components of *Rosa roxburghii* fruit, *Fructus Lycii, Herba Cistanches*, and saffron collected in step 2) had better technical effects than collecting their water-soluble components.

Finally, it should be noted that the above examples are provided merely to describe the technical solutions of the present disclosure, rather than to limit the protection scope of the present disclosure. A person of ordinary skill in the art should understand that modifications or equivalent replacements may be made to the technical solutions of the present disclosure without departing from the spirit and scope of the technical solutions of the present disclosure.

What is claimed is:

1. A preparation method of a medicine composition for boosting immunity, wherein the medicine composition for boosting immunity comprises the following components in parts by weight: 5 parts to 15 parts of Exocarpium *Citri Grandis,* 10 parts to 30 parts of dried tangerine peel, 5 parts to 20 parts of *Rhizoma Atractylodis,* 10 parts to 15 parts of *Rosa roxburghii* fruit, 10 parts to 30 parts of *Fructus Lycii,* 15 parts to 25 parts of *Herba Cistanches*, and 5 parts to 15 parts of saffron; and the preparation method comprises:
 1) Crushing the Exocarpium *Citri Grandis*, the dried tangerine peel, and the *Rhizoma Atractylodis* to obtain a powder 1, conducting extraction with an 80% to 95% ethanol solution, and then conducting filtration to obtain an alcohol extract;
 2) Crushing the *Rosa roxburghii* fruit, the *Fructus Lycii*, the *Herba Cistanches*, and the saffron to obtain a powder 2, conducting extraction with water, adding ethanol to form a system to allow alcohol precipitation, and then collecting an obtained supernatant; and
 3) Combining the alcohol extract obtained in step 1) and the supernatant obtained in step 2), and then drying an obtained mixture to obtain the medicine composition for boosting immunity.

2. The preparation method according to claim 1, wherein the crushing in steps 1) and 2) is conducted to a particle size of 100 mesh to 300 mesh.

3. The preparation method according to claim 1, wherein the ethanol solution and the powder 1 are at a volume-to-mass ratio of 5-20 mL:1 g, and the extraction is conducted at 10° C. to 40° C. for 10 h to 60 h in step 1).

4. The preparation method according to claim 1, wherein the water and the powder 2 are at a volume-to-mass ratio of 5-30 mL:1 g, and the extraction is conducted at 40° C. to 80° C. for 1 h to 5 h in step 2).

5. The preparation method according to claim 1, wherein the ethanol in the system obtained during the alcohol precipitation in step 2) has a volume concentration of 60% to 90%.

* * * * *